(12) United States Patent
Betsill

(10) Patent No.: US 7,422,723 B1
(45) Date of Patent: Sep. 9, 2008

(54) ALCOHOL BREATH TEST DEVICE

(75) Inventor: Harry Edwards Betsill, Parkton, MD (US)

(73) Assignee: Alcohol Detection Systems, Inc., Baltimore, MD (US)

( * ) Notice: Subject to any disclaimer, the term of this patent is extended or adjusted under 35 U.S.C. 154(b) by 796 days.

(21) Appl. No.: 10/693,114

(22) Filed: Oct. 24, 2003

(51) Int. Cl.
  *G01N 33/00* (2006.01)

(52) U.S. Cl. .............................. 422/84; 422/83; 422/90; 422/91; 422/92; 422/104

(58) Field of Classification Search .................. 422/50, 422/83, 98, 84, 90, 91, 92, 104
  See application file for complete search history.

(56) References Cited

U.S. PATENT DOCUMENTS

| | | | | |
|---|---|---|---|---|
| 3,613,665 A | 10/1971 | Gorsuch | ..................... | 128/2 R |
| 3,622,278 A | 11/1971 | Elzinga et al. | ............ | 23/232 R |
| 3,661,528 A | 5/1972 | Falk | ........................ | 23/254 R |
| 3,764,270 A | 10/1973 | Collier et al. | ............. | 23/255 E |
| 3,886,929 A | 6/1975 | Hoppesch et al. | ........... | 128/2 C |
| 3,940,251 A | 2/1976 | Jones et al. | ................ | 23/254 E |
| 3,966,579 A | 6/1976 | Chang et al. | ............. | 204/195 R |
| 4,093,945 A | 6/1978 | Collier et al. | ............... | 340/279 |
| 4,132,109 A | 1/1979 | VanderSyde | .................. | 73/23 |
| 4,248,245 A | 2/1981 | Kempin | ....................... | 128/719 |
| 4,297,871 A | 11/1981 | Wright et al. | ................. | 73/23 |
| 4,300,384 A | 11/1981 | Wiesner et al. | ................ | 73/23 |
| 4,487,055 A | 12/1984 | Wolf | ............................. | 73/23 |
| 4,697,666 A | 10/1987 | Collier et al. | ............... | 180/272 |
| 4,707,336 A | 11/1987 | Jones | .......................... | 422/84 |
| 4,736,619 A | 4/1988 | Legrand | ........................ | 73/23 |
| 4,770,026 A | 9/1988 | Wolf | ............................ | 73/23 |
| 4,868,545 A | 9/1989 | Jones | ......................... | 340/573 |
| 4,901,058 A | 2/1990 | Comeau et al. | ............ | 340/576 |
| 4,912,458 A | 3/1990 | Comeau et al. | ............ | 340/576 |
| 4,914,038 A | 4/1990 | Jewitt | ......................... | 436/132 |
| 4,926,164 A | 5/1990 | Porter et al. | ................ | 340/576 |
| 4,976,135 A | 12/1990 | Stock | ......................... | 73/23.2 |
| 5,020,628 A | 6/1991 | Bigliardi | .................... | 180/272 |
| 5,055,268 A | 10/1991 | Martin | ........................ | 422/84 |
| 5,069,220 A | 12/1991 | Casparie et al. | ............. | 128/719 |
| 5,291,898 A | 3/1994 | Wolf | ........................... | 128/719 |
| 5,303,575 A | 4/1994 | Brown et al. | ................. | 73/23.3 |
| 5,321,972 A | 6/1994 | Stock | ......................... | 73/23.2 |
| 5,393,495 A | 2/1995 | Forrester | ...................... | 422/83 |
| 5,426,415 A | 6/1995 | Prachar et al. | .............. | 340/576 |
| 5,458,853 A | 10/1995 | Porter et al. | ................. | 422/84 |
| 5,496,740 A | 3/1996 | Williams | .................... | 436/132 |
| 5,573,005 A | 11/1996 | Ueda et al. | .................. | 128/730 |
| 5,929,319 A | 7/1999 | King et al. | ................... | 73/23.3 |
| 6,026,674 A | 2/2000 | Gammenthaler | ........... | 73/19.01 |
| 6,167,746 B1 | 1/2001 | Gammenthaler | ........... | 73/19.01 |
| 6,289,718 B1 | 9/2001 | Stock | ......................... | 73/23.2 |

*Primary Examiner*—Sam P Siefke
(74) *Attorney, Agent, or Firm*—Hooker & Habib, P.C.

(57) ABSTRACT

A breath alcohol detection device includes a one-piece multi-passage block with attached sensors, a valve and a fuel cell. The cell accurately determines the BrAC of a prospective vehicle operator. In the event the BrAC is less than the legal maximum for a territory, the device unlocks an ignition interlock to permit starting of the engine and operation of the vehicle.

17 Claims, 3 Drawing Sheets

ALCOHOL BREATH TEST DEVICE

FIELD OF THE INVENTION

The invention relates to breath alcohol detection devices and methods for determining the concentration of alcohol in breath exhaled by a prospective operator of a motor vehicle.

BACKGROUND OF THE INVENTION

Breath alcohol detection devices typically include a computer system for determining breath test results and storing information concerning breath tests for subsequent retrieval, a handheld measurement module connected to the computer system for conducting the test and an ignition interlock which deactivates the vehicle ignition unless a breath test determines that the breath alcohol content (BrAC) of the prospective operator is less than a specified limit. A breath test is performed by connecting a breath tube to the module and having the prospective operator blow breath through the tube and into the module for a sufficient length of time to assure alveolar air has been flowed to the module. A breath test is then conducted on alveolar air to determine the BrAC of the prospective operator.

Many conventional alcohol breath test devices use vacuum pumps to draw breath to be sampled into a detector to determine the BrAC of the prospective operator. These devices include multi-part alcohol modules including the pump and are complicated and expensive.

U.S. Pat. No. 6,167,746 discloses a breath alcohol detection device in which breath is flowed through an induction tube. A sample of the breath in the tube is flowed into a fuel cell to determine the BrAC of the person being tested. Flow to the fuel cell is controlled by opening and closing a valve. A computer system determines the interval the valve is opened based on the pressure in the induction tube after the valve is opened so that a required volume of breath is flowed into the cell.

Accordingly, there is a need for an alcohol breath test device having an improved alcohol measurement module. The module should be made from a single body of rigid material, preferably plastic. Passages required for flowing breath and sample portions of breath should be formed by molding or milling of the body to eliminate manufacturing and assembly cost. The body should support the fuel cell and sensors required to conduct the breath test yet should be sufficiently small to form part of a handheld module easily held by a prospective operator in order to conduct a breath test. The module with the improved block should be resistant to tampering by the prospective operator. There is also a need for an alcohol detection device where the test is performed without creating a pressure pulse which signals to the prospective operator that the test is being taken. There is also a need for a compact alcohol detection device with components mounted in a compact body.

SUMMARY OF THE INVENTION

The invention is an alcohol breath test device with an improved alcohol measurement module adapted to be mounted on a motor vehicle and related method for conducting a breath test. The device includes a computer system, an ignition interlock and an alcohol measurement module.

The ignition interlock normally prevents starting of the vehicle engine but is deactivated by the computer system to permit starting of the engine and operation of the vehicle after a prospective operator successfully passes a breath alcohol test. The alcohol measurement module includes a compact one-piece sensor block containing passages for receiving breath exhaled by the prospective operator taking a breath test and flowing alveolar air into a fuel cell for detecting the BrAC of the prospective operator. Miniature sensors, a valve and a fuel cell are mounted in the block. The block is surrounded by a protective cover having an opening to receive a breath tube permitting flowing of breath into the block. The cover closely surrounds the sensor block and components to prevent tampering by the prospective operator.

In order to conduct a breath test the prospective operator is first required to exhale sufficient breath, at least 1½ liters, to assure exhalation of alveolar breath into the sensor block. A pressure sensor then measures the pressure in an inlet passage in the block. Based on this pressure the computer calculates a valve open interval and then opens a valve leading from the inlet passage to a fuel cell for the interval to flow a small volume of alveolar breath into the fuel cell. The fuel cell generates a voltage output responsive to the volume of ethyl alcohol in the breath sample flowed into the cell. The peak output voltage is proportional to the amount of alcohol consumed by the cell and to the BrAC of the prospective operator taking the breath test. The computer system then calculates the BrAC and deactivates the interlock if the BrAC is below a specified limit.

Opening of the valve to flow breath into the fuel cell does not alter the pressure in the inlet passage. The valve is open for a short period of time, typically 0.250 seconds or less, during which the pressure in the passage is not varied, despite opening of the passage to the fuel cell. Maintaining the pressure in the passage during the time the valve is open equal to the pressure in the passage before the valve is opened permits accurate determination of the valve open interval based on the pressure in the passage before the valve is opened and does not create a pressure pulse signaling the prospective operator that the test is being taken. The sensor block operates without the necessity of a vacuum pump for drawing breath into a fuel cell.

The sensor block used in the measurement module of the invention is of a one-piece construction eliminating multi-component assemblies used in prior art of breath alcohol detection devices and eliminating the necessity of assembling multi-component devices for testing breath alcohol, thus reducing manufacturing and assembly costs for the invention.

The sensor block is compact and positions the fuel cell in close proximity to the valve and inlet passage to reduce the length of the passage leading from the inlet passage to the fuel cell when the valve is open. The short passage increases the accuracy of the test by flowing breath directly into the fuel cell.

Other objects and features of the invention will become apparent as the description proceeds, especially when taken in conjunction with the accompanying drawings illustrating the invention, of which there are three sheets of drawings and one embodiment.

DESCRIPTION OF THE PREFERRED EMBODIMENT

Figure 1:
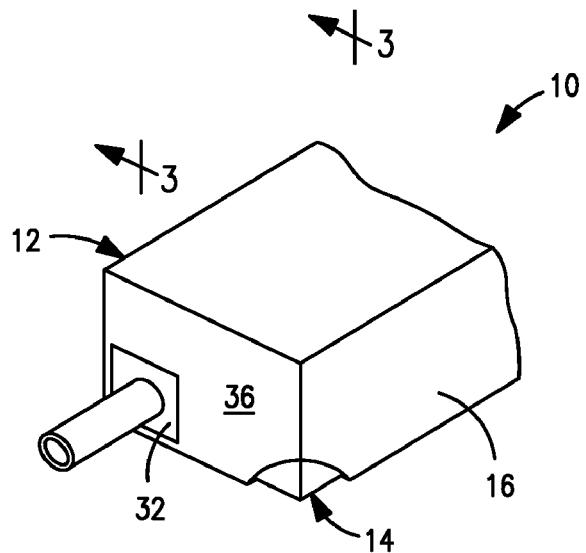
FIG. 1 is a perspective view of a portion of an alcohol measurement module.
Figure 2:
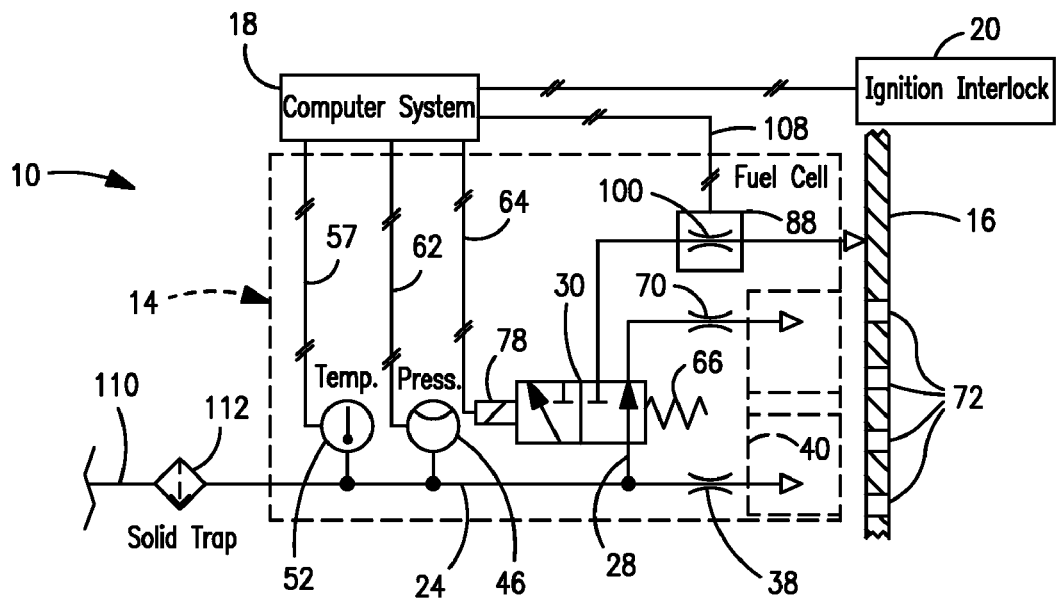
FIG. 2 is a circuit diagram for the breath alcohol detection device.
Figure 3:
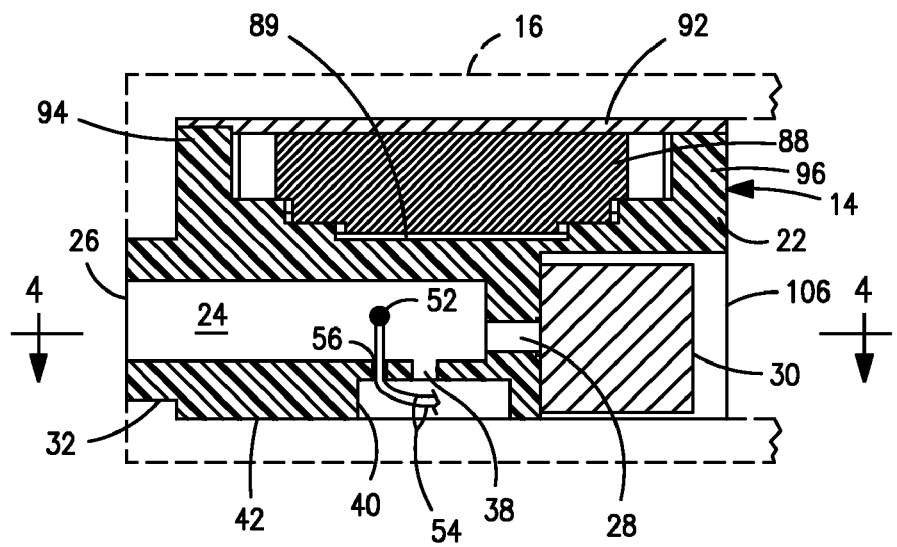
FIG. 3 is a sectional view, partially broken away, taken generally along line 3-3 of FIG. 1.

Breath alcohol detection device 10 includes a hand held alcohol measurement module 12 including a sensor block 14, components on the block and a cover 16 surrounding the block. As illustrated in FIG. 2, device 10 includes a computer system 18 connected to components on block 14 and an ignition interlock 20 for actuating the ignition of a motor vehicle if the breath alcohol content of a prospective operator taking a breath test is less than a specified limit. The interlock defeats the ignition and prevents starting the vehicle if the BrAC equals or exceeds the limit.

Block 14 is preferably machined or molded from a single piece plastic body 22, but may be made of metal or other material if desired. Block 14 includes a breath inlet passage 24 extending from inlet port 26 to outlet port 28 leading to the inlet of two-position solenoid controlled valve 30 mounted in block recess 60. Rectangular collar 32 surrounds inlet port 26 and extends outwardly from block front face 34 through a corresponding rectangular opening formed in cover front wall 36. Vent passage 38 extends from the inner end of inlet passage 24 to enlarged vent recess 40 formed in block bottom face 42. Branch or pressure sensor passage 44 extends from the inner end of passage 24 to pressure sensor 46 mounted in recess 48 formed in block side face 50.

Thermocouple temperature sensor 52 is mounted in the inner end of passage 24 in the path of breath flowed through the passage. The leads 54 for sensor 52 pass through sealed passage 56 extending between passage 24 and recess 40. The leads are routed across the recess and through an open slot 58 in the rear wall of the recess, past valve 30 mounted in cutout or recess 60 in block 14 and rearwardly of the block. Leads 62 for pressure sensor 46 and leads 64 for valve 30 are also led rearwardly of block 14, within cover 16. The leads may be connected to components of computer system 18 located in cover 16 adjacent the block or may be connected to a cable leading from the block, out of cover 16 and to computer system 18.

Figure 4:
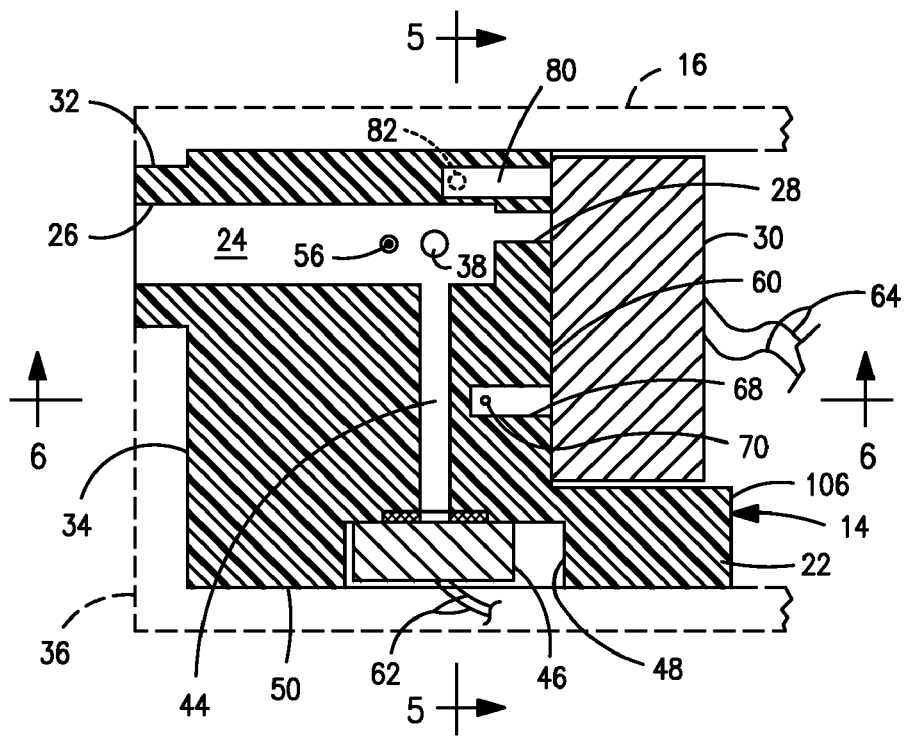
FIG. 4 is a sectional view taken along line 4-4 of FIG. 3.
Figure 6:
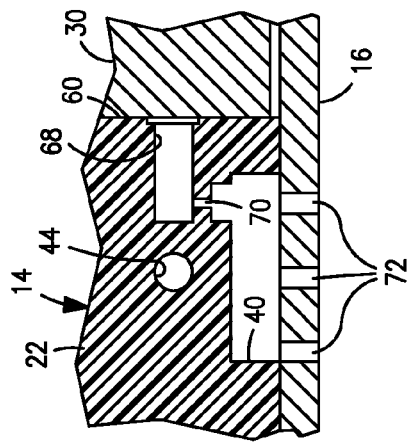
FIG. 6 is a partial sectional view taken along line 6-6 of FIG. 4.
Figure 7:
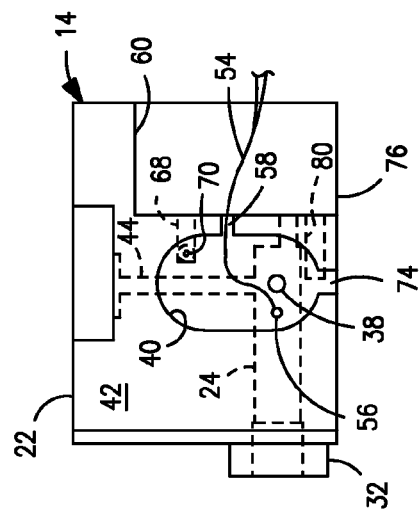
FIG. 7 is a bottom view of a sensor block taken along line 7-7 of FIG. 5.

Outlet port 28 in breath passage 24 communicates with the inlet port of valve 30, as indicated in FIG. 2. Valve 30 includes a spool or valve member (not illustrated) normally biased by spring 66 to communicate the valve inlet port with outlet passage 68 extending a distance from recess 60 into block 14, as shown in FIGS. 4, 6 and 7. Passage 68 communicates with vent recess 40 through small area restriction 70 formed in block 14, shown in FIGS. 4 and 6.

Cover 16 overlies vent recess 40. A plurality of vent passages 72 in the cover overlie the recess to permit venting of breath flowed into the recess to atmosphere. In the event openings 72 are closed or obstructed, breath flowed into recess 40 is vented from the recess through open side slot 58 leading to recess 60 and open side slot 74 leading from the recess to block side face 76 without effecting a breath test.

Figure 5:
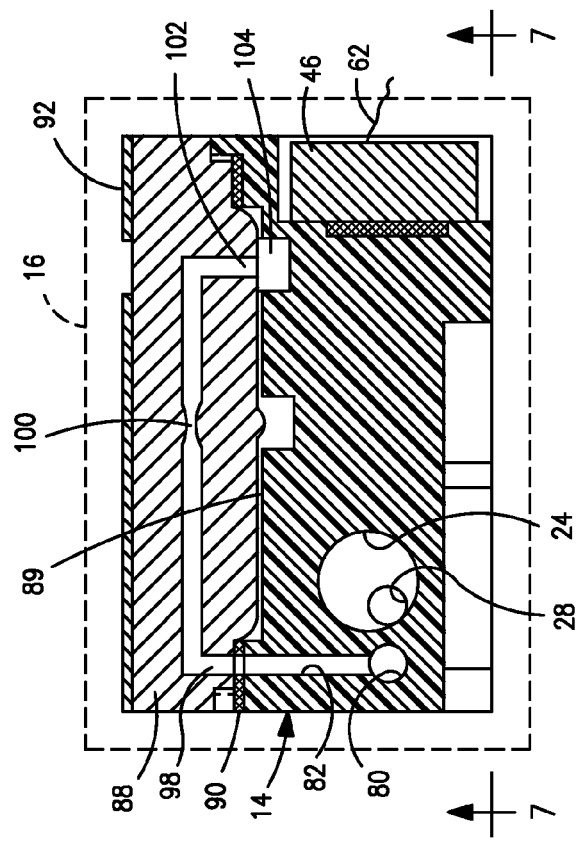
FIG. 5 is a sectional view taken along line 5-5 of FIG. 4.
Figure 8:
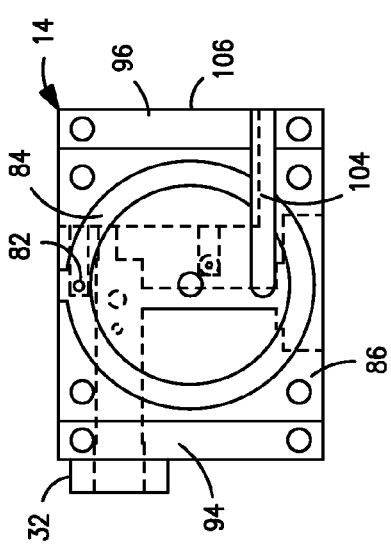
FIG. 8 is a view of the top face of a sensor block.

Valve 30 includes solenoid 78 which is actuated by computer system 18. When the solenoid is actuated the spool of the valve is shifted against spring 66 to a first flow position to connect port 28 to outlet passage 80 shown in FIGS. 4, 5 and 7. Passage 80 extends into block 14 from recess 60 and intersects upwardly extending passage 82. When the solenoid is deactivated, spring 66 shifts the spool to a second flow position connecting port 28 to outlet passage 68. Passage 82 opens through a cylindrical ring 84 located in the top face 86 of block 14.

Alcohol fuel cell 88 is mounted in recess 89 on top face 86 of the block and engages ring gasket 90 seated on ring 84. The fuel cell 88 is held in place on block 14 by cover plate 92 secured to front block wall 94 and rear block wall 96 by suitable fasteners (not illustrated).

The valve 30, sensor 46 and fuel cell 88 are all located in recesses on the sides or faces of block 14 and do not protrude out from the block. These components are substantially at or below the surface of the block. Recessing of components into the block minimizes the physical size of the module 12 and facilitates inserting the module into the cover, removing the module from the cover and holding of module 12.

The fuel cell 88 illustrated diagrammatically includes an inlet port 98 which communicates with outlet passage 82 through a flow opening in gasket 90. The cell has an interior flow passage into a sample volume followed by a restriction 100 and an outlet port 102 on the bottom of the cell. Port 102 communicates with an outlet slot or passage 104 in block 14 extending from port 102 to block rear face 106.

Fuel cell 88 may be the type manufactured by Guth Laboratories, Inc. of Harrisburg, Pa. The fuel cell includes a chemical material which oxidizes ethyl alcohol contained in breath air flowed into the fuel cell and generates an output voltage having a peak value directly proportional to the volume of alcohol consumed. The sample of breath air flowed into the cell to generate a voltage output proportional to breath alcohol content, which may be very small. Samples of 1.2 ml or less are typical. The output of cell 88 is linear during the useful life of the cell in module 12. Cell 88 includes a pair of output leads 108 which are connected to computer system 18.

During breath testing using device 10 a flexible breath collection tube 110 is inserted into inlet port 26 for passage 24. A trap 112 is typically provided in tube 110 to capture solids entrained with breath flowed through the tube. During the test the prospective operator blows breath through the tube into passage 24.

The pressure of breath flowed into inlet passage 24 is determined by the pressure drop from passage 24 to atmosphere through relatively large main vent passage 38. A small volume of breath flowed into passage 24 flows through port 28 and valve 30 directly to atmosphere through restriction 70 when solenoid 78 is not activated. When the solenoid is activated, a small volume of breath is flowed into fuel cell 88 and gas in the cell from a prior test is vented to atmosphere. Preferably, restrictions 70 and 100 are equal so that shifting of the solenoid valve 30 does not alter the pressure in passage 24 and indicate to the prospective operator that a test is being performed. The flow areas of restrictions 70 and 100 are considerably less than the flow area of main vent passage 38 so that the pressure in passage 24 is largely determined by flow through passage 38. Inlet passage 24 is substantially larger than vent passage 38.

In one embodiment of the invention, the diameter of cylindrical inlet passage 24 is 0.250 inches, the diameter of cylindrical vent passage 38 is 0.081 inches and the diameter of cylindrical small vent passage or restriction 70 is 0.022 inches. Passage 38 has a flow area of 0.005 square inches and restriction 70 has a flow area of 0.00038 square inches. In this embodiment, the main vent passage 38 has an area equal to 10.5 percent of the area of the breath inlet passage. The area of restriction 70, which has substantially the same resistance as restriction 100 in fuel cell 88, is 7.3 percent of the area of vent passage or restriction 38. The valve 30 is fast acting so that shifting of the valve does not alter the pressure in passage 24.

Computer system 18 includes analog-to-digital converters to convert analog temperature signals from sensor 52 to digital signals, to convert analog signals from pressure sensor 46 to digital signals and to convert voltage signals from fuel cell 88 to digital signals.

During the useful life of cell 88, the peak output voltage of the cell is directly proportional to the volume of alcohol presented to and consumed by the cell. However, the output voltage for individual fuel cells 88 may not be the same for the same volume of alcohol presented to and consumed by the cell. For this reason, it is necessary to calibrate device 10 to the output performance of the particular fuel cell 88 in block 14.

Fuel cell calibration is performed by determining the peak output voltage of the particular cell 88 in response to imparting a known volume of breath with a known concentration of alcohol into the cell. The known amount of alcohol is generated using a breath test simulator, a device including a water-alcohol solution in which the alcohol concentration is known and, as a result, the concentration of alcohol in vapor over the solution in equilibrium with the solution at a given temperature is known.

Calibration of the device 10 to the output of the fuel cell is conducted with cell 88 mounted in block 14 as illustrated. Breath test simulator vapor containing a known concentration of alcohol is flowed through passage 24 at a known pressure. Valve 30 is shifted for a known interval to flow simulator vapor containing a known amount of alcohol into fuel cell 88. The alcohol is consumed by the cell which generates an output voltage peak proportional to the amount of alcohol consumed. The ratio between the output voltage peak and the BrAC for the prospective operator taking the test, based on simulator vapor alcohol concentration, is programmed into computer system 18 so that the system determines the BrAC as a function of the resultant peak fuel cell output voltage.

The device 10 is also calibrated to determine the volume of breath flowed into the fuel cell as a function of the pressure in passage 24 during each breath alcohol test. This calibration is performed using breath test simulator vapor containing a known concentration of alcohol. A number of tests are performed with the breath test simulator vapor at different pressures and with the valve 30 shifted open for different intervals of time. The resultant data permits generation of a lookup table programmed into system 18. The table permits the system to determine the interval for actuating solenoid 78 to shift valve 30 for flowing breath in passage 24 into the fuel cell as a function of the pressure in passage 24 in order to assure a constant, repeatable volume of breath is flowed into the cell independent of the pressure in passage 24. For some fuel cells this volume is about 1.2 ml of breath. The actual volume flowed through the cell need not be determined. For instance, in order to flow constant volume of breath through the fuel cell valve 30 needs to be opened for a shorter interval when pressure in passage 24 is relatively high and for a longer interval when the pressure in passage 24 is relatively low. The lookup table assures that during breath tests a constant volume of breath is flowed into fuel cell 88 independent of the pressure with which the prospective operator being tested is blowing breath into the passage during the test. In one embodiment of the invention, the solenoid may shift valve 30 open for an interval of 0.050 seconds when the pressure in passage 24 is about 22 inches of water and may shift the valve open for an interval of 0.250 seconds when the pressure in the passage is 10 inches of water in order to flow a constant volume of breath through the cell. The duration of the valve open interval is calculated based on pressure in passage 24 before the valve opens.

After calibration of cell 88, the performance characteristics of the cell are entered into computer system 18 so that the system accurately responds to voltage signals received from the cell to generate accurate determinations of BrAC. The computer system calculates the BrAC from the amount of alcohol flowed into the fuel cell.

Breath alcohol tests are conducted using calibrated device 10 by inserting one end of a breath tube in inlet port 26 with a trap 112 in the tube. The computer system is activated and the prospective operator being tested exhales breath through the tube and into passage 24. The pressure drop across vent passage or restriction 38 maintains a pressure in the passage above ambient pressure, which is sensed by pressure sensor 46 and communicated to computer system 18. Temperature sensor 52 determines the temperature of the breath flowed through passage 24. The computer system determines whether the sensed temperature is within a range of temperatures for exhaled breath and will abort the breath test in the event the sensed temperature falls outside of the range.

Accurate breath alcohol determinations are based on the alcohol concentration in exhaled deep lung or alveolar breath. During the breath test, the computer system monitors the pressure in passage 24 and determines when a sufficient volume of breath, one and one-half liters, has been flowed through the passage to assure that alveolar or deep lung air is flowed through the passage. The volume calculation is performed based on sensed pressure in the passage determined by sensor 46 and the duration of exhalation, according to Bernoulli's principle. This function is also calibrated for each sensor to generate a look up table of flow vs. pressure to allow measurement of the total breath volume.

When a sufficient volume of breath has flowed through the passage to assure flow of alveolar air, the computer system actuates solenoid 78 of valve 30 for an interval based on the pressure in passage 24 immediately before actuation, sufficient to flow a repeatable, small volume of alveolar breath through passages 80 and 82, into fuel cell 88.

After the calculated time interval has elapsed, solenoid 78 is deactivated to shift valve 30 to the position shown in FIG. 2 and stop flow of breath to the fuel cell. The pressure vs. time lookup table previously referred to determines the length of the interval during which solenoid 78 is actuated dependent on the pressure in passage 24. The intervals are short, ranging from about 0.050 seconds to about 0.250 seconds. Actuation of solenoid 78 does not vary the pressure in passage 24 and accordingly does not generate a pressure pulse which can be sensed by the prospective operator. The operator receives no indication the test sample is being taken and cannot lower the pressure in passage 24 in an effort to lower the amount of alcohol flowed into the fuel cell and falsely pass the test.

Fuel cell 88 oxidizes the alcohol in the breath sample flowed into the cell to generate an output voltage communicated to the computer system. The computer system measures the peak voltage of this output signal to determine the BrAC for the prospective operator taking the test. In the event the measured BrAC is greater than permitted, ignition interlock 20 remains engaged to prevent starting the vehicle engine. In the event the BrAC is less than permitted, the computer system deactivates the interlock, permitting starting of the vehicle engine.

Alcohol measurement module 12 is designed to prevent tampering by the prospective operator taking the breath alcohol test. The sensor block is confined within closed cover 16 and is inaccessible to the prospective operator. The back of the cover, away from front 36, closely surrounds a cable connecting the module to computer system 18 and cannot be opened by the prospective operator without evidence of tampering.

The prospective operator may obstruct vent openings 72, by placing a hand or fingers over the opening, in an attempt to prevent flow of breath into cell 88. This strategy is ineffective because the breath flowing into cell 88 does not exit into recess 40 but rather exits into the large recess 60 at block rear face 106 at valve 30, a location inaccessible to the prospective operator. Obstruction of openings 72 does not interfere with normal flow of breath through passages or restrictions 38 and 70, which open into the recess. If openings 72 are obstructed, breath flowed into the recess will flow from the recess into the cover through slots 58 and 74. The fit between block 14 and cover 16 is sufficiently loose to permit flow breath from the block into the case.

In breath alcohol detection device 10 the major components of the computer system and the ignition interlock are mounted on the vehicle at locations inaccessible to the prospective operator taking a breath test. The small and compact alcohol measurement module is connected to the computer system by a cable and is normally mounted on the dashboard of the vehicle away from the controls required for operation of the vehicle.

Cover 16 surrounds block 14 and any computer components in module 12. The cover is preferably formed from relatively soft material such as leather or a synthetic fabric to facilitate handling by the prospective operator taking the test. The cover deters tampering with the surrounded block and computer components (if any).

Compact sensor block 14 may be manufactured from plastic material using a computer controlled milling machine or may be molded from plastic resin. Disclosed block 14 manufactured in this way may have a length between the front and rear faces of about 1¾ inches, a height between the top and bottom faces of ⅞ inches and a width of about 1⅜ inches.

While I have illustrated and described a preferred embodiment of my invention, it is understood that this is capable of modification, and I therefore do not wish to be limited to the precise details set forth, but desire to avail myself of such changes and alterations as fall within the purview of the following claims.

I claim:

1. A breath alcohol detection device comprising:
   A) a breath inlet passage having an inlet port;
   B) a pressure sensor in communication with the breath inlet passage to generate a pressure signal responsive to the pressure in the breath inlet passage;
   C) a fuel cell;
   D) a vent passage communicating the breath inlet passage to the atmosphere;
   E) a two position valve having a valve inlet connected to the breath inlet passage between the inlet port and the vent passage, first and second valve outlets, a valve member moveable from a first position connecting the valve inlet to the first outlet and disconnecting the valve inlet from the second valve outlet and a second position connecting the valve inlet to the second valve outlet and disconnecting the valve inlet from the first valve outlet, wherein the valve inlet is always connected to only one of the valve outlets depending upon the position of the valve member;
   F) a first passage extending from the first valve outlet to atmosphere, and a first restriction in such passage;
   G) a second passage extending from the second valve outlet to atmosphere through the fuel cell, and a second restriction in such second passage, said first restriction generally equaling said second restriction; and
   H) an actuator for shifting the valve member from the first position to the second position for a short interval to flow a volume of breath from the breath inlet passage through the valve, along the second passage and into the fuel cell to generate a fuel cell output signal proportional to the alcohol contained in the volume of breath, the actuator normally maintaining the valve member in the first position, wherein a portion of breath flowed through the breath inlet passage continuously flows through the valve and only one of said first or second passages and one of the restrictions so that the pressure in the breath inlet passage does not substantially vary when the valve member shifts between the first and second positions.

2. The breath alcohol detection device as in claim 1 wherein the vent passage has a flow area larger than the flow area of either restriction.

3. The breath alcohol detection device as in claim 2 wherein the flow area of said first restriction is about 7.3 percent of the flow area of the vent passage.

4. The breath alcohol detection device as in claim 3 wherein the flow area of the first restriction is about 0.00038 square inches and the flow area of the vent passage is about 0.0052 square inches.

5. The breath alcohol detection device as in claim 1 including a body, said passages located in said body, a vent recess in the body, said vent passage and first passage opening in said vent recess, and said second passage opening away from said vent recess.

6. The breath alcohol detection device as in claim 5 including a cover on the body, the cover overlying the vent recess, and one or more vent openings in the cover located over the vent recess.

7. The breath alcohol detection device as in claim 1 wherein said interval is about 0.25 seconds, or less.

8. A breath alcohol detection device including a body having an exterior surface; a plurality of recesses formed in the exterior surface including a pressure sensor recess, a valve recess, a fuel cell recess and a vent recess; a pressure sensor in the pressure sensor recess; a two position valve in the valve recess; a fuel cell in the fuel cell recess; a breath inlet passage in the body extending from an inlet port at the body surface to a vent passage in the body; a pressure sensor passage in the body extending from the breath inlet passage to the pressure sensor; said valve having a valve inlet and first and second valve outlets, and a valve member shiftable between a first position connecting the valve inlet and the first valve outlet only and disconnecting the valve inlet from the second valve outlet and a second position connecting the valve inlet and the second valve outlet only and disconnecting the valve inlet from the first valve outlet, the valve inlet connected to the breath inlet passage; a first passage in the body connecting the first valve outlet to the fuel cell; a second passage in the body connecting the second valve outlet to the vent recess; each of said pressure sensor, valve and fuel cell including electrical leads, all of said leads extending away from said body, wherein breath from the breath inlet passage continuously flows through the valve and through either the first passage or the second passage only depending upon the position of the valve member.

9. The breath alcohol detection device as in claim 8 wherein said pressure sensor, valve and fuel cell are located substantially at or below the surface of the body.

10. The breath alcohol detection device as in claim 8 including a cover surrounding said body, said cover overlying said vent recess, and including vent openings in said cover over such recess.

11. The breath alcohol detection device as in claim 10 including a third passage in the body, said third passage extending from the fuel cell to the surface of the body away from the vent recess.

12. The breath alcohol detection device as in claim 10 wherein said body comprises a block and is formed from a plastic material.

13. The breath alcohol detection device as in claim 10 wherein said body includes a number of faces, said pressure sensor, valve and fuel cell located in said body substantially below said faces.

14. The breath alcohol detection device as in claim 8 including a temperature sensor located in said breath inlet passage, said pressure sensor including leads extending through said body and away from said body.

15. The breath alcohol detection device as in claim 8 including an actuator for shifting the valve member to connect the valve inlet to the first valve outlet for about 0.25 seconds, or less.

16. The breath alcohol detection device as in claim 8 including an actuator to shift the valve member from the first position to the second position for a short interval of time to flow breath from the vent passage through the fuel cell during the interval.

17. The breath alcohol detection device as in claim 8 including a first restriction in the fuel cell and a second restriction in the second passage, said first restriction generally equaling said second restriction.

* * * * *